(12) United States Patent
Rampf et al.

(10) Patent No.: US 10,414,688 B2
(45) Date of Patent: Sep. 17, 2019

(54) METHOD FOR THE PREPARATION OF GLASSES AND GLASS CERAMICS WITH SIO2 AS MAIN CRYSTAL PHASE

(71) Applicant: Ivoclar Vivadent AG, Schaan (LI)

(72) Inventors: Markus Rampf, Lachen (CH); Sebastian Krolikowski, Lachen (CH); Christian Ritzberger, Grabs (CH); Wolfram Höland, Schaan (LI); Marcel Schweiger, Chur (CH)

(73) Assignee: Ivoclat Vivadent AG, Schaan (LI)

( * ) Notice: Subject to any disclaimer, the term of this patent is extended or adjusted under 35 U.S.C. 154(b) by 93 days.

(21) Appl. No.: 15/524,420

(22) PCT Filed: Oct. 28, 2016

(86) PCT No.: PCT/EP2016/076132
§ 371 (c)(1),
(2) Date: May 4, 2017

(87) PCT Pub. No.: WO2017/080853
PCT Pub. Date: May 18, 2017

(65) Prior Publication Data
US 2018/0282204 A1    Oct. 4, 2018

(30) Foreign Application Priority Data
Nov. 11, 2015   (EP) .................................... 15194120

(51) Int. Cl.
*C03C 10/00* (2006.01)
*A61C 13/083* (2006.01)
(Continued)

(52) U.S. Cl.
CPC ............ *C03C 10/0009* (2013.01); *A61C 5/20* (2017.02); *A61C 5/70* (2017.02); *A61C 8/0048* (2013.01);
(Continued)

(58) Field of Classification Search
CPC ..... C03C 10/16; C03C 10/00; C03C 10/0009; C03C 3/087
See application file for complete search history.

(56) References Cited

U.S. PATENT DOCUMENTS 5,632,942 A * 5/1997 Yeh .......................... C04B 35/01
                                                              156/89.17
5,804,520 A * 9/1998 Morinaga ............... C03C 10/16
                                                              501/4

(Continued)

FOREIGN PATENT DOCUMENTS

CA         2252660 A1    5/1999
CA         2942864 A1    10/2015
(Continued)

OTHER PUBLICATIONS

International Preliminary Report on Patentability of PCT/EP2016/076132, dated May 15, 2018, 10 pages.
(Continued)

*Primary Examiner* — Noah S Wiese
(74) *Attorney, Agent, or Firm* — Ann M. Knab; Thad McMurray

(57) ABSTRACT

The invention relates to a method for the preparation of a glass ceramic or a glass, which comprise cerium ions and are suitable in particular for the preparation of dental restorations, the fluorescence properties of which largely correspond to those of natural teeth.
The invention also relates to a glass ceramic and a glass which can be obtained using the method according to the invention, the use thereof as dental material and in particular for the preparation of dental restorations, as well as a glass-forming composition which is suitable for use in the method according to the invention.

18 Claims, 2 Drawing Sheets

(51) Int. Cl.
| | |
|---|---|
| C03C 3/095 | (2006.01) |
| C03C 4/00 | (2006.01) |
| C03C 4/02 | (2006.01) |
| C03C 4/12 | (2006.01) |
| A61C 5/70 | (2017.01) |
| A61C 5/20 | (2017.01) |
| A61C 8/00 | (2006.01) |
| A61C 13/00 | (2006.01) |
| A61C 13/08 | (2006.01) |
| A61C 13/271 | (2006.01) |
| C03C 3/097 | (2006.01) |

(52) U.S. Cl.
CPC ........ *A61C 13/0022* (2013.01); *A61C 13/082* (2013.01); *A61C 13/083* (2013.01); *A61C 13/26* (2013.01); *C03C 3/095* (2013.01); *C03C 3/097* (2013.01); *C03C 4/0021* (2013.01); *C03C 4/02* (2013.01); *C03C 4/12* (2013.01); *C03C 10/0027* (2013.01); *A61C 2201/002* (2013.01); *C03C 2204/00* (2013.01)

(56) References Cited

U.S. PATENT DOCUMENTS 5,902,665 A * 5/1999 Kuroda .................. C03C 3/087
346/137

7,589,038 B2 * 9/2009 Goto .................. C03C 10/0027
428/846.9
2003/0099062 A1 5/2003 Kataoka et al.
2017/0088456 A1 3/2017 Rampf et al.

FOREIGN PATENT DOCUMENTS

| CA | 2944409 A1 | 11/2015 |
|---|---|---|
| EP | 0231773 A1 | 8/1987 |

OTHER PUBLICATIONS

Dittmer, Marc Dr., "Glasses and glass-ceramics in the system of MgO—Al2O3—SiO2 with ZrO2 as nucleating agent," Dissertation, University of Jena, Germany, 2011.
Bei, J., et al., "Optical properties of Ce3+-doped oxide glasses and correlations with optical basicity," Materials Research Bulletin, 42 (2007) pp. 1195-1200. Elsevier Ltd.
Rukmani et al., "Effects of V and Mn Colorants on the Crystallization Behavior and Optical Properties of Ce-Doped Li-Disilicate Glass-Ceramics," J. Am. Ceram. Soc., 90 (3) pp. 706-711 (2007).
Buchalla, W., "Comparative Fluorescence Spectroscopy Shows Differences in Noncavitated Enamel Lesions," Caries Research, 2005, 39, pp. 150-156.
Höland, W. et al, Glass-Ceramic Technology, Second Edition, Jul. 2012, pp. 272-273, Wiley.

* cited by examiner

METHOD FOR THE PREPARATION OF GLASSES AND GLASS CERAMICS WITH SIO2 AS MAIN CRYSTAL PHASE

CROSS-REFERENCE TO RELATED APPLICATIONS

This application is a National Stage application of International patent application PCT/EP2016/076132 filed on Oct. 28, 2016, which claims priority to European patent application No. 15194120.0 filed on Nov. 11, 2015, the disclosures of which are incorporated herein by reference in their entirety.

TECHNICAL FIELD

The present invention relates to a method for the preparation of a glass or a glass ceramic, which contain cerium ions and are suitable in particular for the preparation of dental restorations, the fluorescence properties of which largely correspond to those of natural teeth. The invention also relates to a glass and a glass ceramic, which can be obtained using the method according to the invention, and the use thereof as dental material and in particular for the preparation of dental restorations.

BACKGROUND OF THE INVENTION

Glass ceramics with quartz-like crystals are already known from the state of the art. They are usually glass ceramics with so-called high quartz mixed crystals. These crystals contain different additional ions in the $SiO_2$ framework silicate, which allow this particular type of crystal to have a metastable existence even at room temperature. If these ions were not contained in the glass ceramic, the high quartz formed at high temperatures in the glass ceramic would change into low quartz at 573° C. Holand and Beall describe that glass ceramics with crystals in the high quartz structure have the particular property of low thermal expansion or even of zero expansion within a large temperature range ("Glass-Ceramic Technology" 2nd edition, Wiley, 2012, 272-273). For such glass ceramics, linear coefficients of thermal expansion (CTE) of less than $1.5 \cdot 10^{-6} K^{-1}$ (within the temperature range of 20 to 700° C.) are usually measured. Even glass ceramics with a negative coefficient of expansion can be provided with the aid of the high quartz structure.

Further, lithium disilicate glass ceramics are known from EP 0 916 625 A1, which contain lithium disilicate as main crystal phase and, because of their high translucence and very good mechanical properties, are used particularly in the dental field and primarily for the preparation of crowns and bridges.

From W. Buchalla, "Comparative Fluorescence Spectroscopy Shows Differences in Non-Cavitated Enamel Lesions", Caries Res. 2005, 39, 150-156, it is known that natural teeth display a bluish-white fluorescence with wavelengths in the range of from 400 to 650 nm under ultraviolet light.

Rukmani et al., J. Am. Ceram. Soc. 2007, 90, 706-711, describe the influence of V and Mn colorants on the crystallization behaviour and the optical properties of Ce-doped lithium disilicate glass ceramics. To prepare the glass ceramics, a mixture of the starting materials $SiO_2$, $ZrO_2$, $Li_2CO_3$, $K_2CO_3$, $MgCO_3$ and $Al(PO_3)_3$ is mixed with $CeO_2$, $V_2O_5$ and $MnO_2$, the mixture is melted at 1500° C. in platinum crucibles, cooled and then subjected to several heat treatments in a tube furnace with air supply.

However, it has been shown that the glass ceramics known from the state of the art have insufficient fluorescence properties and cannot imitate the fluorescence properties of natural tooth material to a sufficient extent, in particular under UV light. Dental restorations prepared from such glass ceramics thereby become recognizable as restorations, in particular under the influence of UV light, or are perceived as tooth gaps or defects.

BRIEF DESCRIPTION OF THE DRAWINGS

Further advantages, details and features may be taken from the following description of several exemplary embodiments of the invention in conjunction with the drawings, in which.

SUMMARY OF THE INVENTION

Figure 1:
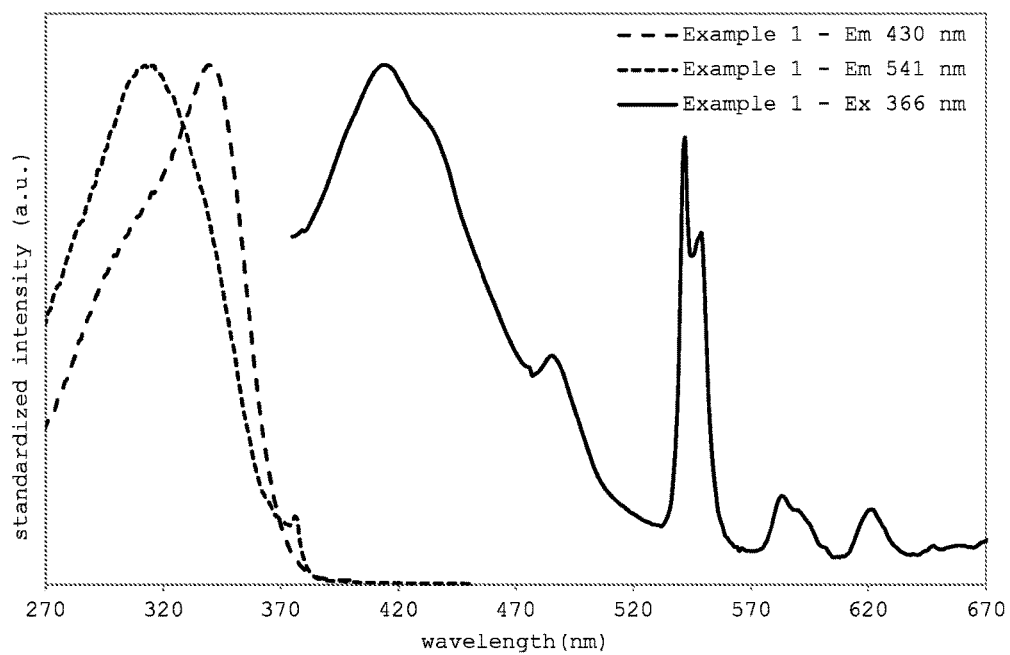
FIG. 1 shows the emission spectrum for the glass ceramic sample in Example 1.

The object of the invention is to provide a glass ceramic which displays a fluorescence comparable to natural tooth material in addition to a high strength and a high coefficient of thermal expansion and is suitable for the preparation of dental restorations which can largely imitate the colour and fluorescence properties of natural tooth material, in particular even under UV light. The glass ceramic should further be easy to be processed, in particular by machining, to form dental restorations and thus be suitable as restorative dental material in an excellent manner. It would be desirable if the glass ceramic could also be given the desired shape by means of hot pressing.

DESCRIPTION OF THE INVENTION

This object is achieved according to the invention by a method for the preparation of a glass ceramic with $SiO_2$ as main crystal phase or a glass which comprises nuclei for the crystallization of $SiO_2$, which comprises a step in which a melt of a starting glass which comprises cerium ions is exposed to reducing conditions.

It has surprisingly been shown that the method according to the invention makes it possible to prepare glass ceramics and glasses which display fluorescence properties that are improved compared with the state of the art, in particular under the action of UV light.

Without being limited to a particular theory, it is assumed that an equilibrium between $Ce^{3+}$ ions and $Ce^{4+}$ ions is established in glass melts which contain cerium ions. It is further assumed that the reducing conditions to which the starting glass is exposed in the method according to the invention shift this ratio in favour of $Ce^{3+}$ ions, which display a fluorescence in the wavelength range of from 320 to 500 nm because of 5d→4f transitions. This fluorescence is particularly suitable for imitating the fluorescence properties of natural tooth material.

Usually the method according to the invention includes reacting the melt of the starting glass with at least one reducing agent. In principle, all agents which are capable of reducing $Ce^{4+}$ ions to $Ce^{3+}$ ions under the conditions of the method according to the invention come into consideration as reducing agents. Those reducing agents which can be removed from the glass melt residue-free after the reduction are preferred.

In particular, gaseous reducing agents as well as reducing agents which, under the conditions of the method according to the invention, are burnt out of the glass melt after the reduction, are preferred. Examples of gaseous reducing agents are gases which comprise hydrogen and preferably mixtures of hydrogen and nitrogen. Examples of reducing agents are furthermore substances which comprise at least one oxidizable carbon atom, in particular carbon, for example graphite, organic salts, carbohydrates and cereal flours.

According to a preferred embodiment the melt of the starting glass is formed from a glass-forming composition which comprises $SiO_2$, $Li_2O$, optionally nucleating agents, a cerium compound and at least one reducing agent. A compound which comprises at least one oxidizable carbon atom and is preferably selected from the group consisting of organic salts, carbohydrates and cereal flours is preferred as the at least one reducing agent. Examples of particularly suitable organic salts are acetylacetonates.

In a particularly preferred embodiment a cerium acetylacetonate, in particular cerium(III) acetylacetonate, is used as reducing agent. According to this embodiment the cerium compound represents at the same time the at least one reducing agent.

According to a further preferred embodiment the at least one reducing agent is a reducing gas, wherein the gas preferably comprises hydrogen and preferably comprises hydrogen and nitrogen. Mixtures of hydrogen and nitrogen which comprise about 5 vol.-% hydrogen and are also called forming gas are particularly suitable. The extent of the reduction can be controlled via the quantity of the gas supplied and in particular via the flow rate and duration of the supply of the gas. The quantity of the active component of the reducing gas, preferably hydrogen, is preferably 0.05 to 5 l/min, in particular 0.1 to 1 l/min and preferably 0.2 to 0.5 l/min, for a period of from 10 to 180 min, in particular 20 to 120 min and preferably 30 to 90 min.

It is preferred according to the invention that the starting glass comprises 0.1 to 7.0 wt.-%, in particular 0.5 to 5.0 wt.-% and preferably 1.0 to 4.0 wt.-% cerium ions, calculated as $CeO_2$.

According to a particularly preferred embodiment the melt of the starting glass is formed from a glass-forming composition which comprises at least one cerium(III) compound and at least one cerium(IV) compound. The ratio of $Ce^{3+}$ ions and $Ce^{4+}$ ions in the obtained glass or glass ceramic can additionally be adjusted by varying the ratio of cerium(III) compound to cerium(IV) compound. In addition, $Ce^{4+}$ ions bring about a yellowing of the glass or glass ceramic material. Thus a particularly good imitation of the fluorescence and colour properties of natural tooth material is made possible. In a particularly preferred embodiment the glass-forming composition comprises 0.1 to 5.0 wt.-%, in particular 0.5 to 3.0 and preferably 1.5 to 2.0 wt.-% cerium (III) compound, calculated as $Ce_2O_3$, and 0.1 to 5.0 wt.-%, in particular 0.5 to 3.0 and preferably 1.5 to 2.0 wt.-% cerium(IV) compound, calculated as $CeO_2$. It is further preferred that the mass ratio of cerium(III) compound, calculated as $Ce_2O_3$, to cerium(IV) compound, calculated as $CeO_2$, lies in the range of from 5:1 to 1:5, in particular 2:1 to 1:2 and preferably 1.25:1 to 1:1.25.

In a particular embodiment the starting glass furthermore comprises terbium ions. The starting glass preferably comprises 0.05 to 2.0, in particular 0.1 to 1.5, preferably 0.2 to 1.0 and particularly preferably 0.3 to 0.7 wt.-% terbium ions, calculated as $Tb_4O_7$. It has surprisingly been shown that according to the invention it is possible, by combining cerium ions and terbium ions, to obtain glasses and glass ceramics, the fluorescence and colour properties of which can imitate those of natural tooth material particularly well. It is particularly surprising that in the case of the glasses and glass ceramics according to the invention the fluorescence brought about by the cerium ions is largely maintained even in the presence of terbium ions, although a reduction or even complete disappearance of the fluorescence brought about by cerium ions was observed in the presence of d-block elements in the state of the art.

The starting glass furthermore comprises at least the component $SiO_2$ necessary for forming a $SiO_2$ crystal phase.

The starting glass usually comprises the following components

| Component | wt. % |
|---|---|
| $SiO_2$ | 58.0 to 92.0 |
| $Li_2O$ | 2.0 to 10.0 |

A glass ceramic prepared from this starting glass surprisingly displays an advantageous combination of mechanical and optical properties desirable for a restorative dental material, and it can also be given the desired shape in a manner desirable for a dental material.

The starting glass preferably comprises 60.0 to 90.0, preferably 70.0 to 83.0 wt.-% and particularly preferably 71.0 to 78.0 wt.-% $SiO_2$.

It is further preferred that the starting glass comprises 2.8 to 9.5, in particular 5.0 to 9.0 and particularly preferably 7.0 to 7.8 wt.-% $Li_2O$. $Li_2O$ serves to improve the meltability of the starting glasses. Further, it also promotes the mobility of the ions in the glass matrix, and it is assumed that this has a positive effect on the crystallization of some crystal phases, e.g. of low quartz and lithium silicate.

It is also preferred that the starting glass, in addition to $Li_2O$, comprises further alkali metal oxide $Me^I_2O$ in a quantity of 0 to 13.0, in particular 1.0 to 13.0 and particularly preferably 2.0 to 13.0 wt.-%. The term "further alkali metal oxide $Me^I_2O$" denotes alkali metal oxide with the exception of $Li_2O$, wherein this $Me^I_2O$ is selected in particular from $K_2O$, $Na_2O$, $Cs_2O$ and/or $Rb_2O$. The starting glass particularly preferably comprises at least one and in particular all of the following further alkali metal oxides $Me^I_2O$ in the given quantities:

| Component | wt. % |
|---|---|
| $K_2O$ | 0 to 5.0 |
| $Na_2O$ | 0 to 3.0 |
| $Cs_2O$ | 0 to 13.0 |
| $Rb_2O$ | 0 to 7.0. |

In a particularly preferred embodiment, the starting glass comprises 1.0 to 4.0 wt.-% $K_2O$.

In addition, it is preferred that the starting glass comprises 0 to 11.0 and in particular 1.0 to 7.0 wt.-% oxide of divalent elements $Me^{II}O$, wherein this oxide $Me^{II}O$ is selected in particular from MgO, CaO, SrO and/or ZnO. The starting glass particularly preferably comprises at least one and in particular all of the following oxides of divalent elements $Me^{II}O$ in the given quantities:

| Component | wt. % |
| --- | --- |
| MgO | 0 to 7.0 |
| CaO | 0 to 4.5 |
| SrO | 0 to 5.0 |
| ZnO | 0 to 4.0. |

In a particularly preferred embodiment, the starting glass comprises 0.5 to 7.0, preferably 1.0 to 5.0 and particularly preferably 1.0 to 3.0 wt.-% MgO and/or 1.0 to 5.0, preferably 1.0 to 4.0 and particularly preferably 2.0 to 4.0 wt.-% CaO.

Furthermore, a starting glass is preferred which comprises 0 to 10.0 and in particular 2.0 to 9.0 wt.-% oxide of trivalent elements $Me^{III}_2O_3$, wherein this $Me^{III}_2O_3$ is selected in particular from $Al_2O_3$, $Y_2O_3$, $La_2O_3$, $B_2O_3$, $Ga_2O_3$ and/or $In_2O_3$. The starting glass particularly preferably comprises at least one and in particular all of the following oxides of trivalent elements $Me^{III}_2O_3$ in the given quantities:

| Component | wt. % |
| --- | --- |
| $Al_2O_3$ | 0 to 8.0 |
| $Y_2O_3$ | 0 to 4.0 |
| $La_2O_3$ | 0 to 2.0 |
| $B_2O_3$ | 0 to 5.0 |
| $Ga_2O_3$ | 0 to 2.0 |
| $In_2O_3$ | 0 to 1.0. |

In a particularly preferred embodiment, the starting glass comprises 1.0 to 8.0, in particular 2.0 to 7.0 and preferably 3.0 to 6.0 wt.-% $Al_2O_3$.

Furthermore, a starting glass is preferred which comprises further oxide of tetravalent elements $Me^{IV}O_2$ in a quantity of 0 to 21.0 wt.-%. The term "further oxide of tetravalent elements $Me^{IV}O_2$" denotes tetravalent oxides with the exception of $SiO_2$ and $CeO_2$, wherein this $Me^{IV}O_2$ is selected in particular from $ZrO_2$, $GeO_2$, $TiO_2$ and/or $SnO_2$. The starting glass particularly preferably comprises at least one and in particular all of the following further oxides of tetravalent elements $Me^{IV}O_2$ in the given quantities:

| Component | wt. % |
| --- | --- |
| $ZrO_2$ | 0 to 11.0 |
| $GeO_2$ | 0 to 21.0 |
| $TiO_2$ | 0 to 5.0 |
| $SnO_2$ | 0 to 3.0. |

In a further preferred embodiment, the starting glass comprises 0 to 7.0, in particular 0 to 6.5, particularly preferably 1.0 to 6.5 and quite particularly preferably 2.0 to 5.0 wt.-% $P_2O_5$. $P_2O_5$ can act as nucleating agent. However, the presence of a nucleating agent is not absolutely necessary for the formation of $SiO_2$ as main crystal phase.

Moreover, a starting glass is preferred which comprises further oxide of pentavalent elements $M^V_2O_5$ in a quantity of 0 to 6.0 and in particular 0 to 5.0 wt.-%. The term "further oxide of pentavalent elements $M^V_2O_5$" denotes pentavalent oxides with the exception of $P_2O_5$, wherein this $M^V_2O_5$ is selected in particular from $V_2O_5$, $Ta_2O_5$ and/or $Nb_2O_5$. The starting glass particularly preferably comprises at least one and in particular all of the following further oxides of pentavalent elements $Me^V_2O_5$ in the given quantities:

| Component | wt. % |
| --- | --- |
| $V_2O_5$ | 0 to 6.0 |
| $Ta_2O_5$ | 0 to 5.0 |
| $Nb_2O_5$ | 0 to 5.0. |

A starting glass is also preferred which comprises 0 to 6.0 wt.-% oxide of hexavalent elements $Me^{VI}O_3$, wherein this $Me^{VI}O_3$ is selected in particular from $WO_3$ and/or $MoO_3$. The starting glass particularly preferably comprises at least one and in particular all of the following oxides $Me^{VI}O_3$ in the given quantities:

| Component | wt. % |
| --- | --- |
| $WO_3$ | 0 to 6.0 |
| $MoO_3$ | 0 to 5.0. |

In addition, a starting glass is preferred which comprises 0 to 5.0 and in particular 0 to 1.0 wt.-% fluorine.

A starting glass which comprises at least one and preferably all of the following components in the given quantities is particularly preferred:

| Component | wt. % |
| --- | --- |
| $SiO_2$ | 58.0 to 92.0 |
| $Li_2O$ | 2.0 to 10.0 |
| $CeO_2$ | 0.1 to 7.0 |
| $Tb_4O_7$ | 0 to 2.0 |
| $Me^I_2O$ | 0 to 13.0 |
| $Me^{II}O$ | 0 to 11.0 |
| $Me^{III}_2O_3$ | 0 to 10.0 |
| $Me^{IV}O_2$ | 0 to 21.0 |
| $P_2O_5$ | 0 to 7.0 |
| $Me^V_2O_5$ | 0 to 6.0 |
| $Me^{VI}O_3$ | 0 to 6.0 |
| fluorine | 0 to 5.0, | wherein $Me^I_2O$, $Me^{II}O$, $Me^{III}_2O_3$, $Me^{IV}O_2$, $Me^V_2O_5$ and $Me^{VI}O_3$ have the above-specified meaning.

In a further particularly preferred embodiment, the starting glass comprises at least one and preferably all of the following components:

| Component | wt. % |
| --- | --- |
| $SiO_2$ | 60.0 to 90.0 |
| $Li_2O$ | 2.8 to 9.5 |
| $CeO_2$ | 0.5 to 5.0 |
| $Tb_4O_7$ | 0.1 to 1.5 |
| $K_2O$ | 0 to 5.0 |
| $Na_2O$ | 0 to 3.0 |
| $Cs_2O$ | 0 to 13.0 |
| $Rb_2O$ | 0 to 7.0 |
| MgO | 0 to 7.0 |
| CaO | 0 to 4.5 |
| SrO | 0 to 5.0 |
| ZnO | 0 to 4.0 |
| $Al_2O_3$ | 0 to 8.0 |
| $Y_2O_3$ | 0 to 4.0 |
| $La_2O_3$ | 0 to 2.0 |
| $B_2O_3$ | 0 to 5.0 |
| $Ga_2O_3$ | 0 to 2.0 |
| $In_2O_3$ | 0 to 1.0 |
| $ZrO_2$ | 0 to 11.0 |
| $GeO_2$ | 0 to 21.0 |
| $TiO_2$ | 0 to 5.0 |
| $SnO_2$ | 0 to 3.0 |
| $P_2O_5$ | 0 to 6.5 |

-continued

| Component | wt. % |
| --- | --- |
| $V_2O_5$ | 0 to 6.0 |
| $Ta_2O_5$ | 0 to 5.0 |
| $Nb_2O_5$ | 0 to 5.0 |
| $WO_3$ | 0 to 6.0 |
| $MoO_3$ | 0 to 5.0 |
| fluorine | 0 to 1.0. |

Some of the above-named components can serve as colorants and/or fluorescent agents. The starting glass can in addition also comprise further colorants and/or fluorescent agents, which can be selected in particular from inorganic pigments and/or oxides of d-block and f-block elements, such as the oxides of Sc, Mn, Fe, Co, Pr, Nd, Er, Dy, Gd, Eu and Yb. Metal colloids, e.g. of Ag, Au and Pd, which can in addition also act as nucleating agents, can also be used as further colorants. These metal colloids can be formed e.g. by reduction of corresponding oxides, chlorides or nitrates during the melting and crystallization processes.

The melt of the starting glass is preferably formed at temperatures of in particular 1500 to 1800° C. The procedure is in particular that a mixture of suitable starting materials, such as carbonates, oxides, phosphates and fluorides, is melted at temperatures of from 1500 to 1800° C. for 0.5 to 10 h. Where a gas is used as reducing agent, the gas is passed through the thus-obtained glass melt. To achieve a particularly high homogeneity, the obtained glass melt can then be poured into water in order to form a granular glass material, and the obtained granular material can then be melted again.

The melt can then be poured into moulds to produce blanks of the starting glass, so-called solid glass blanks or monolithic blanks. These monolithic blanks are usually stress-relieved first, e.g. by keeping them at 450 to 600° C. for 5 to 120 min. This stress relief in the given temperature range usually leads to the formation of nuclei for the crystallization of $SiO_2$ crystal phase and in particular of low quartz crystal phase.

It is likewise possible to put the melt into water again in order to prepare a granular material. This granular material can then be pressed, after grinding and, optionally, addition of further components, to form a blank, a so-called powder compact. Finally, the starting glass can also be processed to form a powder after granulation.

It is likewise possible to put the melt into water again in order to prepare a frit, i.e. a granular material. This frit can be pressed, after grinding and, optionally, addition of further components, such as binders and/or colorants and fluorescent agents, to form a blank, a so-called powder compact.

Finally, the starting glass can also be processed to form a powder after the production of a glass frit.

The glass with nuclei can then be produced from the starting glass by heat treatment. This is also called nucleation process.

In a preferred embodiment for the preparation of the glass with nuclei for the crystallization of $SiO_2$, in particular of low quartz, the starting glass is subjected to a heat treatment at a temperature of from 450 to 600° C. and in particular 500 to 550° C. for a period of in particular from 5 to 120 min and preferably 10 to 40 min.

The glass ceramic according to the invention can then be formed from the glass with nuclei by heat treatment.

In a preferred embodiment for the preparation of the glass ceramic according to the invention, the starting glass or in particular the glass with nuclei is subjected to at least one heat treatment at a temperature of from 700 to 950° C. for a period of in particular 5 to 40 min and preferably 10 to 30 min.

The starting glass or the glass with nuclei can be subjected to the at least one heat treatment e.g. in the form of a solid glass blank or a powder compact.

The at least one heat treatment can also take place during a hot pressing, in particular of a solid glass blank, or during a sintering-on, in particular of a powder.

A preferred embodiment for the preparation of the glass ceramic according to the invention thus represents a method, wherein (a) powder of the starting glass or of the glass with nuclei, optionally after the addition of further components, such as pressing auxiliaries, colorants and/or fluorescent agents, is pressed to form a powder compact, and (b) the powder compact is subjected to a heat treatment at a temperature of from 700 to 950° C. for a period of in particular 5 to 40 min.

A further preferred embodiment for the preparation of the glass ceramic according to the invention represents a method, wherein (a') melt of the starting glass is shaped to form a glass blank, in particular by pouring into a mould, and (b') the glass blank is subjected to a heat treatment at a temperature of from 700 to 900° C. for a period of in particular 5 to 40 min.

In both preferred embodiments of the method a further above-described nucleation can be carried out before the heat treatment in step (b) or (b').

The properties of the glass ceramic are substantially influenced by the main crystal phase. The glass ceramic according to the invention comprises $SiO_2$ as main crystal phase. In a preferred embodiment, the glass ceramic according to the invention comprises low quartz, cristobalite or a mixture thereof, preferably low quartz or cristobalite and particularly preferably low quartz, as main crystal phase.

The term "main crystal phase" denotes the crystal phase which has the highest proportion by mass of all the crystal phases present in the glass ceramic. The masses of the crystal phases are determined in particular using the Rietveld method. A suitable method for the quantitative analysis of the crystal phases using the Rietveld method is described e.g. in M. Dittmer's doctoral thesis "Glaser and Glaskeramiken im System $MgO$—$Al_2O_3$—$SiO_2$ mit $ZrO_2$ als Keimbildner" [Glasses and glass ceramics in the $MgO$—$Al_2O_3$—$SiO_2$ system with $ZrO_2$ as nucleating agent], University of Jena 2011.

It is further preferred that the glass ceramic according to the invention comprises 5.0 to 50.0 and in particular 10.0 to 30.0 wt.-% $SiO_2$ as crystal phase, in particular in the form of low quartz, cristobalite or mixtures thereof.

The glass ceramic according to the invention can comprise, in addition to $SiO_2$ as main crystal phase, also further crystal phases, such as in particular lithium phosphate and/or lithium silicate. Still further nanoscale phases in amorphous or crystalline form can likewise also be present in the glass ceramic according to the invention.

It is preferred that the glass ceramic according to the invention comprises 5.0 to 30.0 and in particular 10.0 to 25.0 wt.-% lithium disilicate.

The type and the amount of the crystal phases formed can be controlled in particular by the composition of the starting glass as well as the heat treatment which is used to prepare the glass ceramic from the starting glass. The examples illustrate this by varying the composition and the heat treatment used.

The glass ceramic according to the invention usually has a coefficient of thermal expansion CTE (measured in the range of from 100 to 500° C.) of at least $5.0 \cdot 10^{-6}$ K$^{-1}$, preferably 10.0 to $20.0 \cdot 10^{-6}$ K$^{-1}$ and particularly preferably 13.0 to $18.0 \cdot 10^{-6}$ K$^{-1}$. The CTE is determined according to ISO 6872 (2008).

The glass ceramic according to the invention is characterized by a very good chemical resistance. To determine the chemical resistance, the glass ceramic was tested according to ISO standard 6872 (2008) by determining the mass loss during storage in aqueous acetic acid. The glass ceramic according to the invention displayed a mass loss of preferably less than 30 µg/cm$^2$.

Furthermore, the glass ceramic according to the invention is characterized in particular by mechanical properties which allow a particularly simple and quick machining to bring the glass ceramic e.g. into the shape of a dental restoration.

The glass ceramic has a biaxial breaking strength of preferably at least 200 MPa and particularly preferably 200 to 500 MPa. The biaxial breaking strength was determined according to ISO 6872 (2008) (piston-on-three-ball test).

The translucence of the glass ceramic was determined in the form of the contrast value (CR value) according to British Standard BS 5612 and it was preferably 35 to 80.

The invention furthermore relates to a glass which comprises nuclei for the crystallization of SiO$_2$, and a glass ceramic with SiO$_2$ as main crystal phase which can be obtained using the method according to the invention. Preferred embodiments for the glass with nuclei suitable for forming the crystallization of SiO$_2$ and the glass ceramic with SiO$_2$ as main crystal phase result from the preferred embodiments for the method according to the invention described above.

The invention furthermore relates to a glass which comprises nuclei for the crystallization of SiO$_2$ and a glass ceramic with SiO$_2$ as main crystal phase, which have a fluorescence intensity at 420 nm and/or in the wavelength range of from 380 to 460 nm (area under the curve) which is at least 1.5 times, in particular at least 2 times, preferably at least 4 times, particularly preferably at least 6 times, the corresponding fluorescence intensity of a reference sample, wherein the reference sample is obtainable by melting a starting glass with the composition: 74.3 wt.-% SiO$_2$, 7.7 wt.-% Li$_2$O, 3.4 wt.-% K$_2$O, 1.8 wt.-% MgO, 3.3 wt.-% CaO, 4.0 wt.-% Al$_2$O$_3$, 3.6 wt.-% P$_2$O$_5$, 1.5 wt.-% CeO$_2$ and 0.4 wt.-% Tb$_4$O$_7$ on a scale of 200 g from suitable raw materials in a platinum-rhodium crucible at 1650° C. for 1 h, pouring 30 g of the glass melt into a pre-heated mould to produce a glass block, and converting the glass block into a glass ceramic by successive temperature treatments at 530° C. for 20 min and 800° C. for 30 min, wherein the heating rates between the temperature treatments are 30 K/min in each case.

Preferably, the glass and the glass ceramic furthermore have a fluorescence intensity at the wavelength of the maximum of the transition $^5D_4 \rightarrow {}^7F_5$ of Tb$^{3+}$, in particular at 541 nm, and/or in the wavelength range of from 535 to 650 nm, preferably in the wavelength range of from 535 to 555 nm (area under the curve) which is at least 1.5 times, in particular at least 2 times, preferably at least 3 times, particularly preferably at least 4 times, the corresponding fluorescence intensity of a reference sample, wherein the reference sample is obtainable as described above.

Particularly preferred are glasses and glass ceramics which have a fluorescence intensity in the wavelength range of from 375 to 700 nm (area under the curve) which is at least 1.5 times, in particular at least 2 times, preferably at least 3 times, particularly preferably at least 4 times, the corresponding fluorescence intensity of a reference sample, wherein the reference sample is obtainable as described above.

The fluorescence is typically measured using platelets with the dimensions: 17.9 mm×15.9 mm×2 mm, the surface of which has been polished with an APEX grinding wheel (0.5 µm), by means of a fluorescence spectrometer of the FL1039 type (Horiba Jobin Yvon GmbH) with a 450 W xenon lamp, an excitation monochromator (gap width 1 nm, excitation wavelength 366 nm), an emission monochromator (gap width 1.5 nm, scan range 372 to 700 nm, increment 1 nm) and a photomultiplier detector (integration time 1 s) of the PMT 1424M type (Horiba Jobin Yvon GmbH). The platelet is typically placed at an angle of 30° relative to the excitation monochromator and the emission is measured at an angle of 90° relative to the excitation monochromator with an optical 5% Neutral Density Filter.

The invention further relates to a glass which comprises nuclei for the crystallization of SiO$_2$ and a glass ceramic with SiO$_2$ as main crystal phase, which have a whitish-blue fluorescence colour in the CIE colour space.

The glass ceramics according to the invention and the glasses according to the invention are present in particular in the form of powders, granular materials or blanks in any shape and size, e.g. monolithic blanks, such as platelets, cuboids or cylinders, or powder compacts, in unsintered, partly sintered or dense-sintered form. They can easily be further processed in these forms, e.g. to form dental restorations. They can, however, also be present in the form of dental restorations, such as inlays, onlays, crowns, veneers, facets or abutments.

Dental restorations, such as bridges, inlays, onlays, crowns, veneers, facets or abutments, can be prepared from the glass ceramics according to the invention and the glasses according to the invention. The invention therefore relates to the use thereof as dental material and in particular to the use thereof for the preparation of dental restorations. It is preferred that the glass ceramic or the glass is given the shape of the desired dental restoration by pressing or machining.

The pressing is usually carried out under increased pressure and increased temperature. It is preferred that the pressing is carried out at a temperature of from 700 to 1200° C. It is further preferred to carry out the pressing at a pressure of from 10 to 30 bar. During the pressing, the desired change in shape is achieved by viscous flow of the material used. The starting glass and the glass with nuclei according to the invention as well as preferably the glass ceramic according to the invention can be used for the pressing. The glasses and glass ceramics according to the invention can in particular be used in the form of blanks in any shape and size, e.g. solid blanks or powder compacts, e.g. in unsintered, partly sintered or dense-sintered form.

The machining is usually carried out by material removal processes and in particular by milling and/or grinding. It is particularly preferred that the machining is carried out as part of a CAD/CAM process. The starting glass, the glass with nuclei according to the invention, as well as the glass ceramic according to the invention can be used for the machining. The glasses and glass ceramics according to the invention can be used in particular in the form of blanks, e.g. solid blanks or powder compacts, e.g. in unsintered, partly sintered or dense-sintered form. The glass ceramic according to the invention is preferably used for the machining. The glass ceramic according to the invention can also be used in a not yet fully crystallized form which was produced by heat treatment at a lower temperature. This has the advantage that an easier machining and thus the use of simpler equipment for the machining are possible. After the machining of such a partly-crystallized material, the latter is usually subjected to a further heat treatment in order to bring about a further crystallization of $SiO_2$ as crystal phase.

However, the glass ceramics according to the invention and the glasses according to the invention are also suitable as coating material for e.g. ceramics, glass ceramics and metals. The invention is therefore likewise directed towards the use of the glasses according to the invention or the glass ceramics according to the invention for coating in particular ceramics, glass ceramics and metals.

The invention also relates to a method for coating ceramics, glass ceramics and metals, in which glass ceramic according to the invention or glass according to the invention is applied to the ceramic, the glass ceramic or the metal and exposed to a temperature of at least 600° C.

This can take place in particular by sintering-on and preferably by pressing-on. With sintering-on, the glass ceramic or the glass is applied to the material to be coated, such as ceramic, glass ceramic or metal, in the usual way, e.g. as powder, and then sintered. With the preferred pressing-on, glass ceramic according to the invention or glass according to the invention is pressed on, e.g. in the form of powder compacts or monolithic blanks, at an increased temperature of e.g. from 700 to 1200° C. and applying pressure, e.g. 10 to 30 bar. For this, in particular the methods described in EP 231 773 and the press furnace disclosed there can be used. Suitable commercial furnaces are the furnaces of the Programat type from Ivoclar Vivadent AG, Liechtenstein.

Because of the above-described properties of the glass ceramics according to the invention and the glasses according to the invention, these are suitable in particular for use in dentistry. A subject of the invention is therefore also the use of the glass ceramics according to the invention or the glasses according to the invention as dental material and in particular for the preparation of dental restorations or as coating material for dental restorations, such as crowns, bridges and abutments.

The invention therefore also relates to a method for the preparation of a dental restoration, in particular bridge, inlay, onlay, veneer, abutment, partial crown, crown or facet, in which the glass ceramic according to the invention or the glass according to the invention is given the shape of the desired dental restoration by pressing, sintering or machining, in particular as part of a CAD/CAM process.

The invention is explained in more detail below by means of non-limiting examples.

EXAMPLES

A total of 12 glasses and glass ceramics according to the invention with the compositions given in Table I were prepared by melting corresponding starting glasses, followed by heat treatments according to Table II for controlled nucleation and crystallization, wherein in Table I the oxidation states of the given oxides refer to the oxidation states of the raw materials used for melting the starting glasses. The following meanings apply in Table II $T_g$ glass transition temperature $T_S$ and $t_S$ temperature and time used for melting $T_N$ and $t_N$ temperature and time used for nucleation $T_C$ and $t_C$ temperature and time used for crystallization $T_{sint}$ and $t_{sint}$ temperature and time used for sintering.

Examples 1-10: Use of a Reducing Cerium Compound as Reducing Agent

To prepare glasses and glass ceramics using a cerium compound as reducing agent, first starting glasses corresponding to the compositions given in Table I were melted from a mixture of usual raw materials in the platinum crucible at the temperature $T_s$ given in Table II for the period $t_s$, wherein cerium(III) acetylacetonate was used as raw material for the given $Ce_2O_3$ content. By pouring the starting glasses into water, glass frits were prepared which were dried in the drying oven at 150° C.

In the Examples 1 to 8, the dried glass frits were then melted a second time at the temperature $T_s$ for the period $t_s$ for homogenization. The obtained glass melts were then poured into pre-heated graphite moulds to produce glass blocks. The glass blocks were then converted to nuclei-containing glasses and glass ceramics by thermal treatment. The thermal treatments used for controlled nucleation and controlled crystallization are given in Table II.

In the Examples 9 and 10, the dried glass frits were ground in a Retsch mill to a particle size of <90 μm. The glass powder was pressed to form a blank and then sintered. The sintering step also brought about a crystallization of the glass accompanied by the formation of a dense glass ceramic shaped body in addition to the compaction of the material. The thermal treatment used for the sintering is given in Table II.

Example 11: Use of an Organic Compound as Reducing Agent

To prepare glasses and glass ceramics using an organic compound as reducing agent, a starting glass corresponding to the composition given in Table I was first melted from a mixture of usual raw materials with the addition of 1.5 wt.-% saccharose in the platinum crucible at the temperature $T_s$ given in Table II for the period $t_s$. By pouring the starting glass into water, a glass frit was prepared which was dried in the drying oven at 150° C. and then melted a second time at the temperature $T_s$ for the period $t_s$ for homogenization. The obtained glass melt was then poured into pre-heated graphite moulds in order to produce glass blocks.

The glass blocks were then converted to nuclei-containing glasses and glass ceramics by thermal treatment. The thermal treatments used for controlled nucleation and controlled crystallization are given in Table II.

Example 11a: Repetition of Example 11 without Addition of a Reducing Agent (Comparison)

Example 11 was repeated without addition of saccharose. The fluorescence of the sample thus obtained is much lower than in Example 11.

Example 12: Use of Forming Gas as Reducing Agent

To prepare glasses and glass ceramics using forming gas as reducing agent, a starting glass corresponding to the composition given in Table I was first melted from a mixture of usual raw materials in the platinum crucible at the temperature $T_s$ given in Table II for the period $t_s$. By pouring the starting glass into water, a glass frit was prepared which was dried in the drying oven at 150° C. The dried glass frit was melted again at the temperature $T_S$ and about 3 l/min forming gas (95% $N_2$, 5% $H_2$) was passed through the glass melt for 60 min by means of a quartz glass dip tube. The dip tube was then removed from the melt and the melt surface was rinsed with forming gas for about 30 min in order to prevent a reoxidation. The glass melt was then poured into pre-heated steel moulds to produce glass blocks.

The glass blocks were then converted to nuclei-containing glasses and glass ceramics by thermal treatment in a normal oven atmosphere. The thermal treatments used for controlled nucleation and controlled crystallization are given in Table II. No effects of the melting under forming gas on the crystallization and/or crystalline structure were observed.

Example 13: Fluorescence Measurements

Platelets were sawn out of the blocks obtained after nucleation with the aid of a suitable saw (Buehler Isomet 5000) and the surface was polished with an APEX grinding wheel (0.5 μm). The platelets were then subjected to a temperature treatment according to Table II in a Programat furnace (Ivoclar Vivadent AG) for the crystallization. In a further processing step, the platelets were ground to the dimensions 17.9 mm×15.9 mm×2 mm and the surface was polished with an APEX grinding wheel (0.5 μm).

To measure the fluorescence properties, a fluorescence spectrometer of the FL1039 type (Horiba Jobin Yvon GmbH) with an excitation monochromator and an emission monochromator was used. The excitation of the samples was carried out by means of a 450 W xenon lamp. The emission intensity was determined using a photomultiplier detector (PMT) of the PMT 1424M type (Horiba Jobin Yvon GmbH) as pulses per second (counts per second, cps). The calibration of the excitation monochromator was carried out by means of an integrated silicon photodiode. The emission monochromator was calibrated via the position of the water Raman peak. The linearity of the detector in the measurement range was ensured via device-specific correction data sets. The linearity of the excitation intensity was ensured during the determination of the excitation spectra via a mathematical correction of the measured emission intensity via the lamp intensity (division of the measured signal by the reference signal of the integrated silicon photodiode which directly determines the lamp intensity). To protect the detector and in order not to reach the saturation range, a 5% Neutral Density Filter was used in the emission beam path.

The samples were clamped in a solid sample holder in the right-angle mode. To prevent reflections of the excitation light, the samples were rotated by 30° relative to the excitation beam, with the result that only diffusely scattered emission light was detected. All samples were measured using identical spectrometer settings (gap widths 1 nm (excitation monochromator) and 1.5 nm (emission monochromator), scan range 372 to 700 nm, increment 1 nm, integration time 1 s, excitation wavelength 366 nm).

FIG. 1 shows, for the glass ceramic sample obtained according to Example 1, the emission spectrum at an excitation wavelength of 366 nm as well as excitation spectra for emission at 430 nm and 541 nm. The emission spectrum displayed a broad maximum at 420 nm, which is to be attributed to the 5d→4f transition of $Ce^{3+}$. The corresponding excitation spectrum for emission at 430 nm displayed an excitation maximum at 340 nm. Furthermore, the emission spectrum displayed maxima at 483, 541, 585 and 619 nm, which are to be attributed to the transitions $^5D_4 \rightarrow {}^7F_6$, $^7F_5$, $^7F_4$ and $^7F_3$ of $Tb^{3+}$. The associated broad excitation spectrum for emission at 541 nm displayed an excitation maximum at 310 nm. The fluorescence emissions shown in the emission spectrum of FIG. 1 are perceived by the human eye overall as white-blue fluorescence.

Figure 2:
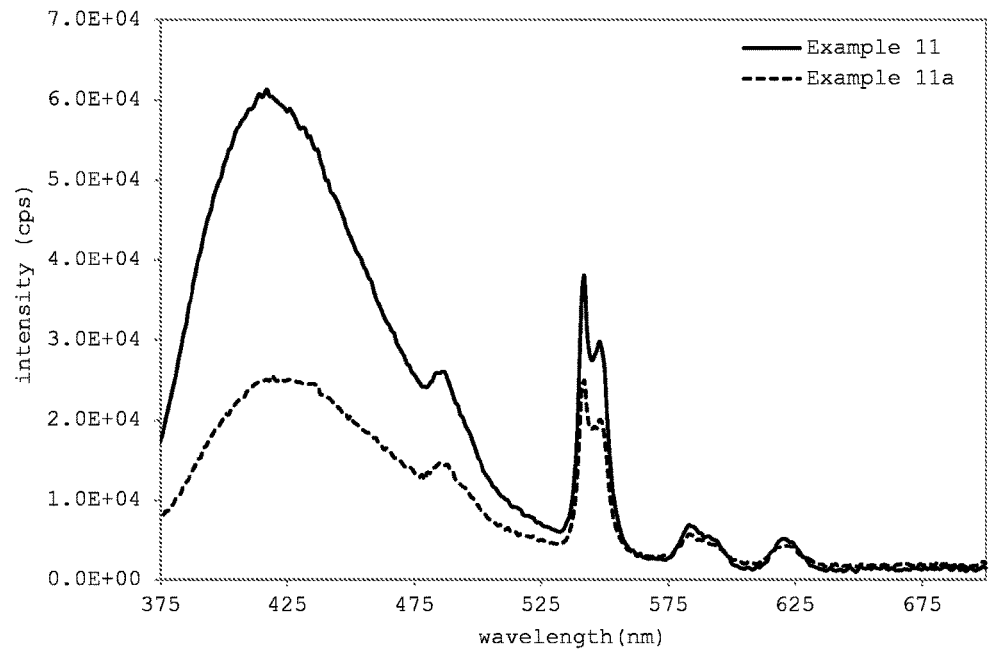
FIG. 2 shows emission spectra obtained at art excitation wavelength of 366 nm for the glass ceramic sample according to Example 11.

FIG. 2 shows emission spectra obtained at an excitation wavelength of 366 nm for the sample according to Example 11, which was prepared under reducing conditions with the addition of saccharose, and the corresponding reference sample of the same composition according to Example 11a which was melted under normal conditions in oxygen-containing atmosphere. The broad emission maximum of $Ce^{3+}$ at about 420 nm and the emission bands of $Tb^{3+}$ at 483, 541, 549, 585 and 619 nm can be seen. A comparison of the spectra shows a clear rise in the intensities of the individual emission bands due to the melting under reducing conditions for the sample according to Example 2. A comparison of the total light emission, determined by calculation of the surface integral under the emission curves over the range of from 375 to 700 nm (total measurement range), shows a rise by a factor of 2.0.

Figure 3:
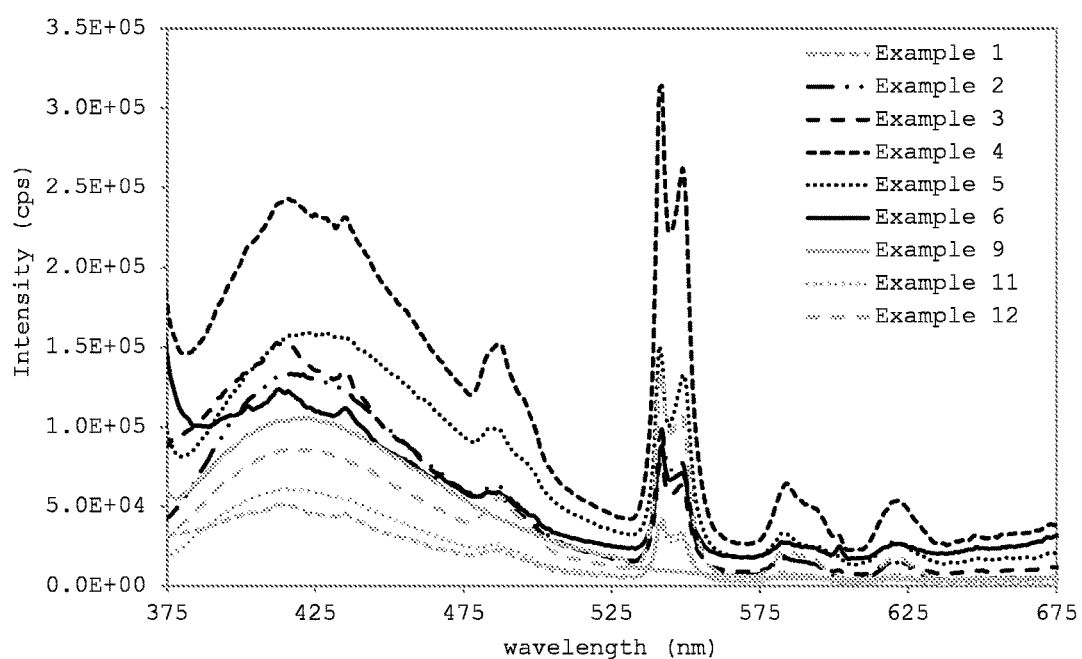
FIG. 3 shows the emission intensities of the samples according to Examples 1-6, 9, 11 and 12.

FIG. 3 shows the emission intensities of the samples according to Examples 1-6, 9, 11 and 12.

TABLE I

| Composition | 1 wt. % | 2 wt. % | 3 wt. % | 4 wt. % | 5 wt. % | 6 wt. % | 7 wt. % | 8 wt. % | 9 wt. % | 10 wt. % | 11 wt. % | 12 wt. % |
|---|---|---|---|---|---|---|---|---|---|---|---|---|
| $SiO_2$ | 74.7 | 72.9 | 71.0 | 71.2 | 72.6 | 70.8 | 78.3 | 85.5 | 77.4 | 60.9 | 74.3 | 75.1 |
| $Li_2O$ | 7.6 | 7.7 | 7.1 | 7.0 | 6.6 | 6.8 | 6.8 | 9.0 | 7.6 | 3.6 | 7.7 | 9.2 |
| $Na_2O$ | — | — | — | — | — | — | — | — | — | 0.5 | — | 2.2 |
| $K_2O$ | 3.4 | 3.5 | 3.6 | 3.2 | 2.3 | 3.2 | 2.0 | — | 3.4 | 3.6 | 3.4 | — |
| $Cs_2O$ | — | — | — | — | 4.9 | — | — | — | — | — | — | — |
| MgO | 1.8 | 1.8 | 2.2 | 4.1 | 0.6 | 1.7 | 1.5 | — | 1.8 | 2.9 | 1.8 | 3.1 |
| CaO | 3.3 | 3.3 | 3.7 | — | — | 2.9 | 2.8 | — | 3.3 | 2.6 | 3.3 | |
| SrO | — | — | — | — | 4.0 | — | — | — | — | — | — | — |
| ZnO | — | — | — | 3.3 | — | — | — | — | — | — | — | — |
| $Al_2O_3$ | 3.8 | 4.1 | 5.6 | 3.7 | 2.6 | 3.3 | 2.0 | — | 3.7 | 4.2 | 4.0 | 3.8 |
| $Y_2O_3$ | — | — | — | — | — | 3.3 | — | — | — | — | — | — |
| $La_2O_3$ | — | — | — | — | — | 1.6 | — | — | — | — | — | — |
| $GeO_2$ | — | — | — | — | — | — | — | — | — | 15.1 | — | — |
| $TiO_2$ | — | — | — | — | — | — | 0.2 | — | — | — | — | — |
| $ZrO_2$ | — | — | — | 1.0 | — | — | 2.0 | — | — | — | — | — |
| $Ce_2O_3$* | 1.4 | 1.7 | 2.7 | 2.8 | 2.6 | 1.9 | 1.5 | 1.9 | 2.8 | 2.0 | — | — |
| $CeO_2$ | — | 0.9 | — | — | — | — | — | — | — | — | 1.5 | 1.5 |
| $P_2O_5$ | 3.6 | 3.6 | 3.7 | 3.3 | 3.4 | 3.4 | 2.8 | 3.2 | — | 4.3 | 3.6 | 4.7 |

TABLE I-continued

| Composition | Example | | | | | | | | | | | |
|---|---|---|---|---|---|---|---|---|---|---|---|---|
| | 1 wt. % | 2 wt. % | 3 wt. % | 4 wt. % | 5 wt. % | 6 wt. % | 7 wt. % | 8 wt. % | 9 wt. % | 10 wt. % | 11 wt. % | 12 wt. % |
| $V_2O_5$ | — | 0.1 | — | — | — | — | — | — | — | — | — | — |
| $Ta_2O_5$ | — | — | — | — | — | 0.7 | — | — | — | — | — | — |
| $Tb_4O_7$ | 0.4 | 0.4 | 0.4 | 0.4 | 0.4 | 0.4 | — | 0.4 | — | 0.3 | 0.4 | 0.4 |
| F | — | — | — | — | — | — | 0.1 | — | — | — | — | — |

*used as cerium(III) acetylacetonate

TABLE II

| | Example | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| $T_g$/° C. | 487 | 469 | 505 | 504 | 488 | 495 | 494 | — | 482 | 464 | 506 | 473 |
| $T_s$/° C. | 1650 | 1650 | 1650 | 1650 | 1680 | 1680 | 1650 | 1680 | 1650 | 1680 | 1650 | 1600 |
| $T_S$/min | 120 | 120 | 120 | 120 | 120 | 120 | 120 | 120 | 180 | 120 | 60 | 120 |
| $T_N$/° C. | 520 | 520 | 530 | 520 | 510 | 520 | 510 | 530 | — | — | 530 | 490 |
| $T_N$/min | 30 | 30 | 30 | 30 | 60 | 20 | 30 | 30 | — | — | 30 | 60 |
| $T_C$/° C. | 800 | 800 | 800 | 810 | 830 | 860 | 760 | 900 | — | — | 800 | 740 |
| $T_C$/min | 30 | 30 | 30 | 30 | 30 | 10 | 30 | 30 | — | — | 30 | 30 |
| $T_{Sint}$/° C. | — | — | — | — | — | — | — | — | 890 | 920 | — | — |
| $t_{Sint}$/min | — | — | — | — | — | — | — | — | 15 | 15 | — | — |
| Main crystal phase | low quartz | low quartz | cristo-balite | cristo-balite | low quartz | cristo-balite | low quartz | low quartz | low quartz | low quartz | low quartz | low quartz |
| Secondary crystal phase | $Li_2Si_2O_5$ $Li_3PO_4$ | $Li_2Si_2O_5$ $Li_3PO_4$ | $Li_2Si_2O_5$ tridymite | $Li_3PO_4$ | $CsAlSi_5O_{12}$ $Li_3PO_4$ $Li_2Si_2O_5$ tridymite | $Li_3PO_4$ $SiO_2$ | $Li_2Si_2O_5$ $Li_3PO_4$ | $Li_3PO_4$ $Li_2Si_2O_5$ | $Li_2Si_2O_5$ | $Li_3PO_4$ cristo-balite $Li_3PO_4$ diopside | $Li_2Si_2O_5$ $Li_3PO_4$ | $Li_2Si_2O_5$ $Li_3PO_4$ |

The invention claimed is:

1. Method for the preparation of a glass ceramic with $SiO_2$ as main crystal phase or a glass which comprises nuclei for the crystallization of $SiO_2$, which comprises a step in which a melt of a starting glass is formed from a glass-forming composition which comprises $SiO_2$, $Li_2O$, a cerium compound and at least one reducing agent.

2. Method according to claim 1, in which the at least one reducing agent is a compound which comprises at least one oxidizable carbon atom.

3. Method according to claim 1, in which the at least one reducing agent is an acetylacetonate.

4. Method according to claim 1, in which the starting glass comprises 0.1 to 7.0 wt.-% cerium ions, calculated as $CeO_2$.

5. Method according to claim 1, in which the starting glass comprises 0 to 11.0 wt.-% alkaline earth metal oxide.

6. Method according to claim 1, in which the starting glass comprises at least one of the following components in the given quantities:

| Component | wt. % |
|---|---|
| $SiO_2$ | 58.0 to 92.0 |
| $Li_2O$ | 2.0 to 10.0 |
| $CeO_2$ | 0.1 to 7.0 |
| $Tb_4O_7$ | 0 to 2.0 |
| $Me^I_2O$ | 0 to 13.0 |
| $Me^{II}O$ | 0 to 11.0 |
| $Me^{III}_2O_3$ | 0 to 10.0 |
| $Me^{IV}O_2$ | 0 to 21.0 |
| $P_2O_5$ | 0 to 7.0 |
| $Me^V_2O_5$ | 0 to 6.0 |
| $Me^{VI}O_3$ | 0 to 6.0 |
| fluorine | 0 to 5.0, | wherein
$Me^I_2O$ is selected from $Na_2O$, $K_2O$, $Rb_2O$ and/or $Cs_2O$,
$Me^{II}O$ is selected from $MgO$, $CaO$, $SrO$ and/or $ZnO$,
$Me^{III}_2O_3$ is selected from $Al_2O_3$, $B_2O_3$, $Y_2O_3$, $La_2O_3$, $Ga_2O_3$ and/or $In_2O_3$,
$Me^{IV}O_2$ is selected from $ZrO_2$, $GeO_2$, $TiO_2$ and/or $SnO_2$,
$Me^V_2O_5$ is selected from $V_2O_3$, $Ta_2O_5$ and/or $Nb_2O_5$ and
$Me^{VI}O_3$ is selected from $WO_3$ and/or $MoO_3$.

7. Method according to claim 1 for the preparation of a glass with nuclei which are suitable for forming low quartz, cristobalite or a mixture thereof.

8. Method according to claim 1 for the preparation of a glass ceramic which has low quartz, cristobalite or a mixture thereof as main crystal phase.

9. Method according to claim 1 for the preparation of a glass ceramic which comprises 5.0 to 50.0 wt.-% $SiO_2$ as crystal phase.

10. Method according to claim 1, in which the starting glass is subjected to at least one heat treatment in the range of from 700° to 950° C.

11. Method according to claim 1, in which the glass ceramic or the glass are present in the form of a powder, a blank or a dental restoration.

12. Method according to claim 2, in which the at least one reducing agent is selected from the group consisting of organic salts, carbohydrates and cereal flours.

13. Method according to claim 4, in which the starting glass comprises 1.0 to 4.0 wt.-% cerium ions, calculated as $CeO_2$.

14. Method according to claim 9 for the preparation of a glass ceramic which comprises 10.0 to 30.0 wt.-% $SiO_2$ as crystal phase.

15. Method for the preparation of a glass ceramic with $SiO_2$ as main crystal phase or a glass which comprises nuclei for the crystallization of $SiO_2$, which comprises a step in which a melt of a starting glass which comprises cerium ions and terbium ions is exposed to reducing conditions.

16. Method according to claim 15, in which the starting glass comprises 0.05 to 2.0 wt.-% terbium ions, calculated as $Tb_4O_7$.

17. Method according to claim 15, in which the starting glass comprises 0.3 to 0.7 wt.-% terbium ions, calculated as $Tb_4O_7$.

18. Method according to claim 5, in which the starting glass comprises 1.0 to 7.0 wt.-% alkaline earth metal oxide.

\* \* \* \* \*